United States Patent [19]

Genain

[11] Patent Number: 4,920,225
[45] Date of Patent: Apr. 24, 1990

[54] RESOLUTION OF 1,4-DIHYDROPYRIDINE DERIVATIVES

[75] Inventor: Gilles Genain, Issy-les-Moulineaux, France

[73] Assignee: Laboratoires Syntex S.A., Puteaux, France

[21] Appl. No.: 945,760

[22] Filed: Dec. 22, 1986

[51] Int. Cl.$^5$ .......................... C07F 9/06; C07F 9/22; C07F 9/28; C07D 215/36; C07D 413/00; C07D 215/16; C07D 215/20; C07D 213/72

[52] U.S. Cl. .................................... 546/21; 546/153; 546/155; 546/157; 546/159; 546/167; 546/257; 546/258; 546/268; 546/269; 546/270; 546/271; 546/273; 546/274; 546/280; 546/283; 546/284; 546/286; 546/287; 546/288; 546/289; 546/291; 546/294; 546/295; 546/296; 546/297; 546/298; 546/299; 546/307; 546/308; 546/309; 546/310; 546/316; 546/318; 546/321; 546/322

[58] Field of Search ............... 546/286, 294, 310, 321, 546/322, 21, 257, 258, 283, 284, 280, 273, 268, 270, 271, 274, 269; 153, 155, 157, 159, 167, 287, 288, 289, 291, 295, 296, 297, 298, 299, 307, 308, 309, 316, 318

[56] References Cited

U.S. PATENT DOCUMENTS

| | | | |
|---|---|---|---|
| 4,264,611 | 4/1981 | Berntsson et al. | 546/286 |
| 4,370,334 | 1/1982 | Sato | 546/310 |
| 4,495,192 | 1/1985 | Muto et al. | 546/310 |
| 4,510,310 | 4/1985 | Wehinger et al. | 546/286 |
| 4,535,073 | 8/1985 | Kimura et al. | 546/286 |
| 4,558,058 | 12/1985 | Schonafinger et al. | 546/310 |
| 4,576,934 | 3/1986 | Set et al. | 546/21 |
| 4,595,690 | 6/1986 | Clark et al. | 546/286 |
| 4,672,071 | 6/1987 | Clark et al. | 546/310 |

FOREIGN PATENT DOCUMENTS

| | | | |
|---|---|---|---|
| 060674 | 9/1982 | European Pat. Off. | 546/286 |
| 161917 | 11/1985 | European Pat. Off. | 546/286 |
| 166296 | 1/1986 | European Pat. Off. | 546/286 |
| 2117761A | 10/1983 | United Kingdom | 546/286 |
| 2122192A | 1/1984 | United Kingdom | 546/286 |

OTHER PUBLICATIONS

T. Shibanuma, *Chem. Pharm. Bull.,* 28, 2809–2812 (1980).
E. Wehinger, *Angew. Chem. Int. Ed. Engl.,* 20, 762–769 (1981).

*Primary Examiner*—Mary C. Lee
*Assistant Examiner*—J. Richter
*Attorney, Agent, or Firm*—Brian Lewis; Tom M. Moran; Alan M. Krubiner

[57] ABSTRACT

Optically active compounds of formula 1

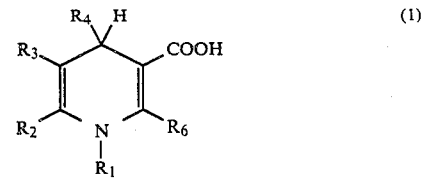

wherein
 $R_1$ is H or lower alkyl;
 $R_2$ and $R_6$ are each independently lower alkyl, aryl, or arylalkyl;
 $R_3$ is CN, $NO_2$, $CO_2R_5$, $CONHR_5$, $SO_2R_5$, or $P(O)(OR_5)_2$, where $R_5$ is lower alkyl, lower alkoxyalkyl, aryl, or arylalkyl;
 $R_4$ is aryl, heterocyclyl, or fused-ring heterocyclyl, optionally substituted with one, two, or three halo, $NO_2$, CN, lower alkyl, lower alkoxy, lower alkylamino, $CF_3$, $OCH_2F$, or $OCF_3$;

are prepared by fractional crystallization from hot organic solvent and water in the presence of a suitable optically active amine base.

3 Claims, No Drawings

RESOLUTION OF 1,4-DIHYDROPYRIDINE DERIVATIVES

BACKGROUND OF THE INVENTION

This invention relates to a method for resolving 1,4-dihydropyridine derivitives into optically active isomers by fractional crystallization, and to optically active 1,4-dihydropyridine derivative salts.

RELATED DISCLOSURES

Certain 4-aryl-1,4-dihydropyridine derivatives are known calcium entry agonists and antagonists. See, for example, U.S. Pat. Nos. 3,485,847, 4,044,141, and 4,595,690. It has been found that resolved optical isomers of dihydropyridine derivatives usually have biological activity which differs from the activity of racemic mixtures thereof. It is known that for many biologically active dihydropyridine derivatives, for example nicardapine, the isomer which has an (S) configuration at C4 in the dihydropyridine ring has greater calcium entry blocking activity than the (R) isomer. The (R) isomer of the compound 2,6-dimethyl-3-nitro-4-(2-trifluoromethylphenyl)-5-carbomethoxy-1,4-dihydropyridine displays calcium entry antagonism, while the (S) isomer is a calcium entry facilitator. It is to be appreciated that calcium entry agonists and calcium entry antagonists are each therapeutic in the appropriate circumstances.

Compounds with the (S) configuration may be prepared from (S)-2,6-dialkyl-3-carboalkoxy-4-aryl-5-carboxy-1,4-dihydropyridine derivatives of formula 1. This (S) isomer has been prepared following the method of T. Shibanuma, et al., *Chem. Pharm. Bull.*, 28, 2809–2812 (1980), by resolving 1-ethoxymethyl-2,6-dimethyl-3-carbomethoxy-4-(3-nitrophenyl)-5-carboxy-1,4-dihydropyridine using cinchonidine in methanol. However, Shibanuma's method requires that one protect the dihydropyridine nitrogen using chloromethyl ethyl ether (a flammable lachrymator) in the presence of sodium hydride, monosaponify, and later remove the protecting group by acid hydrolysis. This protection and deprotection reduces the ultimate yield of resolved dihydropyridine derivative.

Other methods of achieving optical resolution are described in EP 26,317, FR 2,528,431, and FR 2,523,128. These methods avoid the need to protect and deprotect the dihydropyridine nitrogen, but require the addition of special ester groups to achieve derivatives that may be separated. For example, EP 26,317 discloses a method for resolving dihydropyridine derivatives by esterifying a dihydropyridine acid with (R)-2-phenyl-2-methoxyethanol, separating the resulting diastereomers by chromatography, and removing the 2-phenyl-2-methoxyethoxy group to provide the resolved dihydropyridine acid. Of course, each esterification and saponification detracts from the overall yield of the resolution, and chromatographic processes are usually to be avoided in pharmaceutical manufacturing.

I have now discovered a more efficient, effective, and less expensive method for preparing optically active mono-esterified dihydrophyridine derivatives directly, which dispenses with the need for protecting groups and ester groups, and which is easily practiced at an industrial scale. The salts of optically active compounds of formula 1 and optically active amines are useful for preparing calcium entry modulators of therapeutic value

SUMMARY OF THE INVENTION

One aspect of the invention is a method for preparing optically active compounds of formula 1:

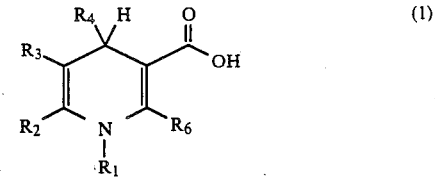

wherein $R_1$ is H or lower alkyl;

$R_2$ and $R_6$ are each independently lower alkyl, aryl, or arylalkyl;

$R_3$ is CN, $NO_2$, $CO_2R_5$, $CONHR_5$, $SO_2R_5$, or $P(O)(OR_5)_2$, where $R_5$ is lower alkyl, lower alkoxyalkyl, aryl, or arylalkyl;

$R_4$ is aryl, heterocyclyl, or fused-ring heterocyclyl, optionally substituted with one, two, or three substituents independently selected from halo, $NO_2$, CN, lower alkyl, lower alkoxy, lower alkylamino, $CF_3$, $OCH_3F$, and $OCF_3$; and addition salts thereof with an optically active amine base, such as cinchonidine, cinchonine, quinine, quinidine, strychnine, brucine, morphine, l-arginine, d-α-phenylethylamine, dehydroabietylamine, cinchonicine, 1-2-amino-1-propanol, d-amphetamine, glucosamine, conessine, or anabasine.

Another aspect of the invention is a salt of an optically active compound of formula 1 with an optically active base:

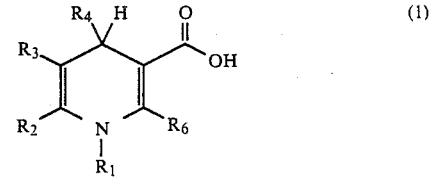

wherein $R_1$ is H or lower alkyl;

$R_2$ and $R_6$ are each independently lower alkyl, aryl, or arylalkyl;

$R_3$ is CN, $NO_2$, $CO_2R_5$, $CONHR_5$, $SO_2R_5$, or $P(O)(OR_5)_2$, where $R_5$ is lower alkyl, lower alkoxyalkyl, aryl, or arylalkyl;

$R_4$ is aryl, heterocyclyl, or fused-ring heterocyclyl, optionally substituted with one, two, or three substituents independently selected from halo, $NO_2$, CN, lower alkyl, lower alkoxy, lower alkylamino, $CF_3$, $OCH_2F$, and $OCF_3$; and said optically active amine base is cinchonidine, cinchonine, quinine, quinidine, strychnine, brucine, morphine, d-α-phenylethylamine, l-arginine, dehydroabietylamine, cinchonicine, 1-2-amino-1-propanol, d-amphetamine, glucosamine, conessine, or anabasine.

DETAILED DESCRIPTION AND PREFERRED EMBODIMENTS

One aspect of the invention is a method for resolving the optical isomers of a compound of formula 1

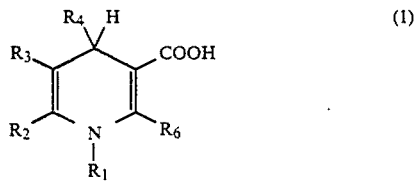

(1)

wherein
- $R_1$ is H or lower alkyl;
- $R_2$ and $R_6$ are each independently lower alkyl, aryl, or arylalkyl;
- $R_3$ is CN, $NO_2$, $CO_2R_5$, $CONHR_5$, $SO_2R_5$, or $P(O)(OR_5)_2$, where $R_5$ is lower alkyl, lower alkoxyalkyl, aryl, or arylalkyl;
- $R_4$ is aryl, heterocyclyl, or fused-ring heterocyclyl, optionally substituted with one, two, or three substituents independently selected from halo, $NO_2$, CN, lower alkyl, lower alkoxy, lower alkylamino, $CF_3$, $OCH_2F$, and $OCF_3$; and
- addition salts thereof with an optically active amine base such as cinchonidine, cinchonine, quinine, quinidine, strychnine, brucine, morphine, l-arginine, d-α-phenylethylamine, dehydroabietylamine, cinchonicine, 1-2-amino-1-propanol, d-amphetamine, glucosamine, conessine, or anabasine; which method comprises dissolving said compound of formula 1 and an optically active amine base in a ratio of about 1:2 to about 2:1, wherein said amine base is cinchonidine, quinidine, strychnine, cinchonine, quinine, brucine, morphine, d-α-phenylethylamine, l-arginine, dehydroabietylamine, cinchonicine, 1-2-amino-1-propanol, d-amphetamine, glucosamine, conessine, or anabasine in a solvent selected from the combination of dimethyl formamide, ethanol, or acetonitrile with water to form a solvent/water salt solution which is about 10% to about 50% water; heating said solution at a temperature between about 50° C. and the reflux temperature of said solvent for about 2 to about 30 minutes to form a racemic salt solution; and allowing one optically active salt of said compound of formula 1 to crystallize. A preferred class of the invention is the method wherein said amine is cinchonidine, cinchonine or quinidine. A preferred subclass of the invention is the method wherein $R_1$ is H, $R_2$ and $R_6$ are methyl, $R_3$ is CN or $CO_2 R_5$ (where $R_5$ is methyl, ethyl, isopropyl, or methoxyethyl), and $R_4$ is phenyl or 2-thienyl, optionally substituted with one, two, or three substituents independently selected from halo, $NO_2$, CN, lower alkyl, lower alkoxy, lower alkylamino, $CF_3$, $OCH_2F$, and $OCF_3$, particularly the method wherein $R_3$ is carbomethoxy and $R_4$ is 3-nitrophenyl.

Another aspect of the invention is the addition salt prepared from an optically active compound of formula 1 with an optically active base, wherein said optically active amine base is cinchonidine, cinchonine, quinine, quinidine, strychnine, brucine, morphine, l-arginine, d-α-phenylethylamine, dehydroabietylamine, conessine, cinchonicine, 1-2-amino-1-propanol, d-amphetamine, glucosamine, or anabasine. A preferred class of the invention is the salt wherein said amine is cinchonidine, cinchonine or quinidine. A preferred subclass of the invention is the salt wherein $R_1$ is H, $R_1$ and $R_6$ are methyl, $R_3$ is cyano, carbomethoxy or carboethoxy, and $R_4$ is 3-nitrophenyl, 2-nitrophenyl, 2-chlorophenyl, or 2,3-dichlorophenyl, particularly the salt wherein $R_3$ is carbomethoxy and $R_4$ is 3-nitrophenyl.

DEFINITIONS

As used in the specification and appended claims unless specified to the contrary, the following terms have the meaning indicated:

The term "lower alkyl" refers to a straight or branched chain monovalent radical consisting solely of carbon and hydrogen, containing no unsaturation and having from one to four carbon atoms. Examples of lower alkyl groups are methyl, ethyl, n-propyl, i-propyl, n-butyl, i-butyl, s-butyl and t-butyl.

The term "alkoxy" refers to a radical of the form $R_aO—$, where $R_a$ is lower alkyl as defined above.

The term "alkoxyalkyl" refers to radicals of the form $—R_b—O—R_a$, where $R_b$ is alkylene of one to six carbon atoms, and $R_a$ is lower alkyl as defined above. Examples of alkoxyalkyl groups are methoxymethyl, methoxyethyl, 1-(2-propoxy)ethyl, t-butoxymethyl, and the like.

The term "halo" as used herein refers to fluoro, chloro, bromo and iodo.

The term "heterocyclyl" as used herein refers to saturated and unsaturated cyclic radicals composed of carbon and hydrogen, with oxygen, nitrogen, and/or sulfur heteroatoms, Heterocyclyl groups as referred to herein are rings of 5 or 6 members. Examples of heterocyclyl groups are 2-thienyl, 2-thiazolyl, 2-furyl, 2-pyridyl, and 3-pyridyl.

Fused-ring heterocyclyl groups are benzo-fused heterocyclyl radicals, such as quinolinyl, benzodioxazolyl, benzo[b]thienyl, benzoxazolyl, benzo[b]furanyl, indolyl, and the like. Fused-ring heterocyclyl radicals may be joined to the dihydropyridine ring through any position.

The term "optionally substituted" includes the cases where a group is substituted or unsubstituted. As used herein, "optionally substituted" heterocyclyl groups may be substituted with zero, one or two lower alkyl, lower alkoxy, $NO_2$, CN, $CF_3$, $OCF_3$, $OCH_2F$, alkylamino, and dialkylamino, as those terms are defined herein. Thus, the term "optionally substituted heterocyclyl radical" includes, for example, 2-methyltetrahydrofuran-4-yl, 2-methoxytetrahydropyran-4-yl, 2-methylfuran-4-yl, and the like.

The term "basic addition salts" refers to salts of the subject compounds formed with organic or inorganic bases. Inorganic bases may be, for example, chloride, bromide, iodide, hydroxide, carbonate, bicarbonate, sulfate, nitrate, and the like. Organic bases may be for example, acetate, benzoate, tosylate, lactate, and the like, and include optically active bases such as cinchonidine, quinidine, strychnine, brucine, morphine, cinchonine, quinine, d-α-phenylethylamine, l-arginine, dehydroabietylamine, cinchonicine, 1-2-amino-1-propanol, d-amphetamine, glucosamine, conessine, anabasine, and the like.

The term "suitable optically active amine base" refers to a basic amine compound having a chiral center which forms an insoluble salt with either the (S) isomer or the (R) isomer of a compound of formula 1 in the solvent selected. Presently preferred optically active bases are cinchonidine, cinchonine, quinidine, and N-alkyl-glucamines, where alkyl includes C1 through C10. The presently most preferred optically active bases are cinchonidine, cinchonine and quinidine.

The term "mineral acid" refers to protic acids which have a $pK_a$ lower than 5. Examples of mineral acids include HCl, HBr, $H_2SO_4$, $HNO_3$, and the like.

The term "soft acid" refers to protic organic acids which have a $pK_a$ higher than mineral acids. Examples of soft acids include acetic acid, oxalic acid, toluic acid, and the like.

The nomenclature used herein is a modified form of the I.U.P.A.C. convention. Compounds of the invention are named as derivatives of 1,4-dihydropyridine. The positions in the compounds are numbered beginning with the pyridine nitrogen and proceeding clockwise in all drawings of the structure. For example, the following compound is named 2,6-dimethyl-3-carbomethoxy-4-(3-nitrophenyl)-5-carboxy-1,4-dihydropyridine:

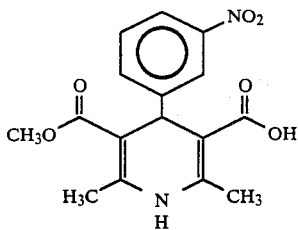

Compounds of formula 1 have a chiral center at C4 in the dihydropyridine ring, and thus can exist as optical isomers. Optical isomers of compounds may be specified (+) or (−), indicating the direction the chiral center rotates a plane of polarized light.

Optically active intermediates and compounds of formula 1 may also be designated using the IUPAC R-S convention, sometimes called the "sequence rule." A description of the R-S convention may be found, for example, in "Introduction to Organic Chemistry" by A. Streitwieser, Jr. and C. Heathcock, (Macmillan Pub. Co., New York, 1976), pages 110–114. For example, the compound depicted below is (S)-2,6-dimethyl-3-(2-propoxycarbonyl)-4-(3-nitrophenyl)-5-carboxy-1,4-dihydropyridine:

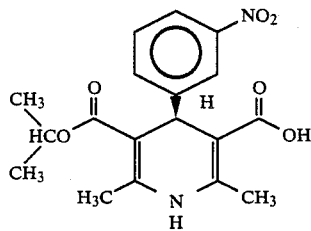

PREPARATION OF THE INVENTION

Optically-resolved compounds and salts of formula 1 are prepared by following the method of the invention. An unresolved compound of formula 1 is first obtained using methods known in the art. For example, one may use the Hantzsch Dihydropyridine synthesis, using reactants selected to provide the desired substitutions for $R_1$, $R_2$, $R_3$, and $R_4$. Compounds wherein $R_3$ is $CO_2R_5$, $NO_2$, CN, or $CONHR_5$ can be prepared by reacting an aryl aldehyde, acetoacetic acid, and a compound of the formula $R_3$—CH=C($NH_2$)$R_2$ under Hantzsch conditions (e.g., refluxing EtOH) to provide an unresolved dihydropyridine derivative. For example, methyl β-aminocrotonate, 3-nitrobenzaldehyde and acetoacetic acid are heated at reflux in ethanol to yield unresolved 2,6-dimethyl-3-methoxycarbonyl-4-(3-nitrophenyl)-5-carboxy-1,4-dihydropyridine. Other unresolved compounds of formula 1 may similarly be prepared by following the teachings of U.S. Pat. No. 4,595,690, incorporated herein by reference in its entirety.

Unresolved compounds of formula 1 in which $R_3$ is $SO_2R_5$ may be similarly prepared, or may be prepared by following the methods taught in U.S. Pat. No. 4,126,321, incorporated herein by reference in full.

Unresolved compounds of formula 1 in which $R_3$ is $P(O)(OR_5)_2$ may similarly be prepared, or may be prepared by following the methods taught in U.S. Pat. Nos. 4,576,934 and 4,535,073, incorporated herein by reference in full.

Once the unresolved compound of formula 1 has been obtained, it is resolved into optically pure isomers by following the method of the instant invention. An amount of a compound of formula 1 is dissolved in a mixture of water and a solvent selected from dimethyl formamide, ethanol, and acetonitrile at a temperature between about 80° C. and the reflux temperature of the mixture, along with an optically active amine in a molar ratio of dihydropyridine to amine of about 1:2 to about 2:1, to produce a solution that is between about 10% to about 50% water. The preferred amount of water depends on which solvent is selected. For DMF, the preferred percentage of water is 30% to 50%, particularly about 40%. For $CH_3CN$, the preferred percentage of water is about 20% to 40%, particularly about 20%. For EtOH, the preferred percentage of water is about 10% to 30%, particularly about 20%. Where the solvent is dimethyl formamide, the water may optionally be added at the next step. When the amount of optically active amine used is less than the amount of dihydropyridine, an inexpensive base such as NaOH or $NH_4OH$ may be used to make up the difference. The optically active amine is, for example, cinchonidine, quinidine, strychnine, brucine, morphine, cinchonine, quinine, d-α-phenylethylamine, l-arginine, conessine, dehydroabietylamine, cinchonicine, l-2-amino-1-propanol, d-amphetamine, glucosamine, or anabasine, with cinchonidine and quinidine being the most preferred.

At this point, the mixture is allowed to stand and cool gradually, so that the salt of one optical isomer of the compound of formula 1 crystallizes from the resolution solution. The crystalline salt is filtered, washed, and dried to yield an optically pure dihydropyridine derivative salt, and the resulting salt recrystallized, e.g. from EtOH. The pure optically active salt may then be cleaved by dissolving it in a dilute strong acid, for example, HCl, $H_2SO_4$, or the like, to yield a pure optically active dihydropyridine acid of formula 1. The other optical isomer may similarly be recovered from the resolution solution.

The resulting optically pure dihydropyridine acid derivatives may be esterified or amidated by means known in the art to produce pharmaceutically active agents which modulate calcium channel activity, and generally affect cerebrovascular and cardiovascular activity. For example, (−)-2,6-dimethyl-3-carbomethoxy-4-(3-nitrophenyl)-5-carboxy-1,4-dihydropyridine may be esterified with 2-(N-methyl-N-benzylamino)e- thanol to yield the (+) optical isomer of 2,6-dimethyl-3-carbomethoxy-4-(3-nitrophenyl)-5-[2-(N-methyl-N-benzylamino)ethoxycarbonyl]-1,4-dihydropyridine, (also known as nicardapine) having the greatest biological activity. Similarly, (−)-2,6-dimethyl-3-carbomethoxy-4-(3-nitrophenyl)-5-carboxy-1,4-dihydropyridine may be esterified with ethanol to yield the optical isomer of 2,6-dimethyl-3-carbomethoxy-4-(3-nitrophenyl)-5-carboethoxy-1,4-dihydropyridine, (also known as nitrendipine) having the greatest biological activity.

The following examples are presented as further illustrations of the practice and preparation of the invention, and are not intended as limitations on the scope of the invention.

EXAMPLE 1

(Preparation of Quinidine Salts)

(A) A mixture of 2,6-dimethyl-3-carbomethoxy-4-(3-nitrophenyl)-5-carboxy-1,4-dihydropyridine (40.0 g, 0.12 mol) and anhydrous quinidine (39 g, 0.12 mol) was dissolved in hot DMF (72 mL). Then, water (48 mL) was added and the solution allowed to cool to room temperature. After 24 hours, the resulting precipitate was filtered, dried, and recrystallized from hot DMF/$H_2O$ (60:40) to afford the quinidine salt (mp=165° C.).

The pure (−) dihydropyridine acid was obtained by dissolving 17.8 g or the quinidinium salt and NaOH (2.7 mL of 35% soln) in water (60 mL). The solution was extracted twice with $CH_2Cl_2$ (30 mL), then acidified with HCl (12N, 3.4 mL). The resulting precipitate was filtered, washed with $H_2O$, and dried. The dried product was rinsed with $Et_2O$ (2×50 mL) to yield pure (−)-2,6-dimethyl-3-carbomethoxy-4-(3-nitrophenyl)-5-carboxy-1,4-dihydropyridine (1), $[\alpha]_D^{20}=-20.4°$ (c=0.5, acetone), mp=200° C.

(B) Similarly, proceeding as in part (A) above but substituting the appropriate starting materials for 2,6-dimethyl-3-carbomethoxy-4-(3-nitrophenyl)-5-carboxy-1,4-dihydropyridine, the following optically resolved compounds are prepared:

2,6-dimethyl-3-carbomethoxy-4-(2-nitrophenyl)-5-carboxy-1,4-dihydropyridine;
2,6-dimethyl-3-carbomethoxy-4-(2-chlorophenyl)-5-carboxy-1,4-dihydropyridine;
(−)-2,6-dimethyl-3-carbomethoxy-4-(3-chlorophenyl)-5-carboxy-1,4-dihydropyridine, mp=210° C., $[\alpha]_D^{20}=-8.0°$, c=5, DMF;
2,6-dimethyl-3-carbomethoxy-4-(2,3-dichlorophenyl)-5-carboxy-1,4-dihydropyridine;
2,6-dimethyl-3-carbomethoxy-4-(4-methylphenyl)-5-carboxy-1,4-dihydropyridine;
2,6-dimethyl-3-carbomethoxy-4-(3-cyanophenyl)-5-carboxy-1,4-dihydropyridine;
2,6-dimethyl-3-carbomethoxy-4-(3-trifluoromethylphenyl)-5-carboxy-1,4-dihydropyridine;
2,6-dimethyl-3-carbomethoxy-4-(3-trifluoromethoxyphenyl)-5-carboxy-1,4-dihydropyridine;
(+)-2,6-dimethyl-3-carbomethoxy-4-(3-methoxyphenyl)-5-carboxy-1,4-dihydropyridine, mp=235° C., $[\alpha]_D^{20}=+1.7°$, c=5, DMF;
(+)-2,6-dimethyl-3-carbomethoxy-4-(2-thienyl)-5-carboxy-1,4-dihydropyridine, mp=200° C., $[\alpha]_D^{20}=+6.5°$, c=5, DMF;
2,6-dimethyl-3-carbomethoxy-4-(5-methylthien-2-yl)-5-carboxy-1,4-dihydropyridine;
2,6-dimethyl-3-carboethoxy-4-(2-nitrophenyl)-5-carboxy-1,4-dihydropyridine;
2,6-dimethyl-3-carboethoxy-4-(3-nitrophenyl)-5-carboxy-1,4-dihydropyridine;
2,6-dimethyl-3-carboethoxy-4-(3-chlorophenyl)-5-carboxy-1,4-dihydropyridine;
2,6-dimethyl-3-carboethoxy-4-(2-chlorophenyl)-5-carboxy-1,4-dihydropyridine;
2,6-dimethyl-3-carboethoxy-4-(2,3-dichlorophenyl)-5-carboxy-1,4-dihydropyridine;
2,6-dimethyl-3-carboethoxy-4-(4-methylphenyl)-5-carboxy-1,4-dihydropyridine;
2,6-dimethyl-3-carboethoxy-4-(3-cyanophenyl)-5-carboxy-1,4-dihydropyridine;
2,6-dimethyl-3-carboethoxy-4-(3-trifluoromethylphenyl)-5-carboxy-1,4-dihydropyridine;
2,6-dimethyl-3-carboethoxy-4-(3-trifluoromethoxyphenyl)-5-carboxy-1,4-dihydropyridine;
2,6-dimethyl-3-carboisopropoxy-4-(2-nitrophenyl)-5-carboxy-1,4-dihydropyridine;
2,6-dimethyl-3-carboisopropoxy-4-(3-nitrophenyl)-5-carboxy-1,4-dihydropyridine;
2,6-dimethyl-3-carboisopropoxy-4-(3-chlorophenyl)-5-carboxy-1,4-dihydropyridine;
2,6-dimethyl-3-carboisopropoxy-4-(2-chlorophenyl)-5-carboxy- 1,4-dihydropyridine;
2,6-dimethyl-3-carboisopropoxy-4-(2,3-dichlorophenyl)-5-carboxy-1,4-dihydropyridine;
2,6-dimethyl-3-carboisopropoxy-4-(4-methylphenyl)-5-carboxy-1,4-dihydropyridine;
2,6-dimethyl-3-carboisopropoxy-4-(3-cyanophenyl)-5-carboxy-1,4-dihydropyridine;
2,6-dimethyl-3-carboisopropoxy-4-(3-trifluoromethylphenyl)-5-carboxy-1,4-dihydropyridine;
2,6-dimethyl-3-carboisopropoxy-4-(3-trifluoromethoxyphenyl)-5-carboxy-1,4-dihydropyridine;
2,6-dimethyl-3-methylsulfonyl-4-(2-nitrophenyl)-5-carboxy-1,4-dihydropyridine;
2,6-dimethyl-3-methylsulfonyl-4-(3-nitrophenyl)-5-carboxy-1,4-dihydropyridine;
2,6-dimethyl-3-methylsulfonyl-4-(3-chlorophenyl)-5-carboxy-1,4-dihydropyridine;
2,6-dimethyl-3-methylsulfonyl-4-(2-chlorophenyl)-5-carboxy-1,4-dihydropyridine;
2,6-dimethyl-3-methylsulfonyl-4-(2,3-dichlorophenyl)-5-carboxy-1,4-dihydropyridine;
2,6-dimethyl-3-methylsulfonyl-4-(4-methylphenyl)-5-carboxy-1,4-dihydropyridine;
2,6-dimethyl-3-methylsulfonyl-4-(3-cyanophenyl)-5-carboxy-1,4-dihydropyridine;
2,6-dimethyl-3-methylsulfonyl-4-(3-trifluoromethylphenyl)-5-carboxy-1,4-dihydropyridine;
2,6-dimethyl-3-methylsulfonyl-4-(3-trifluoromethoxyphenyl)-5-carboxy-1,4-dihydropyridine;
2,6-dimethyl-3-ethylsulfonyl-4-(2-nitrophenyl)-5-carboxy-1,4-dihydropyridine;
2,6-dimethyl-3-ethylsulfonyl-4-(3-nitrophenyl)-5-carboxy-1,4-dihydropyridine;
2,6-dimethyl-3-ethylsulfonyl-4-(3-chlorophenyl)-5-carboxy-1,4-dihydropyridine;
2,6-dimethyl-3-ethylsulfonyl-4-(2-chlorophenyl)-5-carboxy-1,4-dihydropyridine;
2,6-dimethyl-3-ethylsulfonyl-4-(2,3-dichlorophenyl)-5-carboxy-1,4-dihydropyridine;
2,6-dimethyl-3-ethylsulfonyl-4-(4-methylphenyl)-5-carboxy-1,4-dihydropyridine;
2,6-dimethyl-3-ethylsulfonyl-4-(3-cyanophenyl)-5-carboxy-1,4-dihydropyridine;

2,6-dimethyl-3-ethylsulfonyl-4-(3-trifluoromethylphenyl)-5-carboxy-1,4-dihydropyridine;
2,6-dimethyl-3-ethylsulfonyl-4-(3-trifluoromethoxyphenyl)-5-carboxy-1,4-dihydropyridine;
2,6-dimethyl-3-isopropylsulfonyl-4-(2-nitrophenyl)-5-carboxy-1,4-dihydropyridine;
2,6-dimethyl-3-isopropylsulfonyl-4-(3-nitrophenyl)-5-carboxy-1,4-dihydropyridine;
2,6-dimethyl-3-isopropylsulfonyl-4-(3-chlorophenyl)-5-carboxy-1,4-dihydropyridine;
2,6-dimethyl-3-isopropylsulfonyl-4-(2-chlorophenyl)-5-carboxy-1,4-dihydropyridine;
2,6-dimethyl-3-isopropylsulfonyl-4-(2,3-dichlorophenyl)-5-carboxy-1,4-dihydropyridine;
2,6-dimethyl-3-isopropylsulfonyl-4-(4-methylphenyl)-5-carboxy-1,4-dihydropyridine;
2,6-dimethyl-3-isopropylsulfonyl-4-(3-cyanophenyl)-5-carboxy-1,4-dihydropyridine;
2,6-dimethyl-3-isopropylsulfonyl-4-(3-trifluoromethylphenyl)-5-carboxy-1,4-dihydropyridine;
2,6-dimethyl-3-isopropylsulfonyl-4-(3-trifluoromethoxyphenyl)-5-carboxy-1,4-dihydropyridine;
2,6-dimethyl-3-dimethylphosphonyl-4-(2-nitrophenyl-5-carboxy-1,4-dihydropyridine;
2,6-dimethyl-3-dimethylphosphonyl-4-(3-nitrophenyl)-5-carboxy-1,4-dihydropyridine;
2,6-dimethyl-3-dimethylphosphonyl-4-(3-chlorophenyl)-5-carboxy-1,4-dihydropyridine;
2,6-dimethyl-3-dimethylphosphonyl-4-(2-chlorophenyl)-5-carboxy-1,4-dihydropyridine;
2,6-dimethyl-3-dimethylphosphonyl-4-(2,3-dichlorophenyl)-5-carboxy-1,4-dihydropyridine;
2,6-dimethyl-3-dimethylphosphonyl-4-(4-methylphenyl)-5-carboxy-1,4-dihydropyridine;
2,6-dimethyl-3-dimethylphosphonyl-4-(3-cyanophenyl)-5-carboxy-1,4-dihydropyridine;
2,6-dimethyl-3-dimethylphosphonyl-4-(3-trifluoromethylphenyl)-5-carboxy-1,4-dihydropyridine;
2,6-dimethyl-3-dimethylphosphonyl-4-(3-trifluoromethoxyphenyl)-5-carboxy-1,4-dihydropyridine;
2,6-dimethyl-3-diethylphosphonyl-4-(2-nitrophenyl)-5-carboxy-1,4-dihydropyridine;
2,6-dimethyl-3-diethylphosphonyl-4-(3-nitrophenyl)-5-carboxy-1,4-dihydropyridine;
2,6-dimethyl-3-diethylphosphonyl-4-(3-chlorophenyl)-5-carboxy-1,4-dihydropyridine;
2,6-dimethyl-3-diethylphosphonyl-4-(2-chlorophenyl)-5-carboxy-1,4-dihydropyridine;
2,6-dimethyl-3-diethylphosphonyl-4-(2,3-dichlorophenyl)-5-carboxy-1,4-dihydropyridine;
2,6-dimethyl-3-diethylphosphonyl-4-(4-methylphenyl)-5-carboxy-1,4-dihydropyridine;
2,6-dimethyl-3-diethylphosphonyl-4-(3-cyanophenyl)-5-carboxy-1,4-dihydropyridine;
2,6-dimethyl-3-diethylphosphonyl-4-(3-trifluoromethylphenyl)-5-carboxy-1,4-dihydropyridine;
2,6-dimethyl-3-diethylphosphonyl-4-(3-trifluoromethoxyphenyl)-5-carboxy-1,4-dihydropyridine;
2,6-dimethyl-3-diisopropylphosphonyl-4-(2-nitrophenyl)-5-carboxy-1,4-dihydropyridine;
2,6-dimethyl-3-diisopropylphosphonyl-4-(3-nitrophenyl)-5-carboxy-1,4-dihydropyridine;
2,6-dimethyl-3-diisopropylphosphonyl-4-(3-chlorophenyl)-5-carboxy-1,4-dihydropyridine;
2,6-dimethyl-3-diisopropylphosphonyl-4-(2-chlorophenyl)-5-carboxy-1,4-dihydropyridine;
2,6-dimethyl-3-diisopropylphosphonyl-4-(2,3-dichlorophenyl)-5-carboxy-1,4-dihydropyridine;
2,6-dimethyl-3-diisopropylphosphonyl-4-(4-methylphenyl)-5-carboxy-1,4-dihydropyridine;
2,6-dimethyl-3-diisopropylphosphonyl-4-(3-cyanophenyl)-5-carboxy-1,4-dihydropyridine;
2,6-dimethyl-3-diisopropylphosphonyl-4-(3-trifluoromethylphenyl)-5-carboxy-1,4-dihydropyridine;
2,6-dimethyl-3-diisopropylphosphonyl-4-(3-trifluoromethoxyphenyl)-5-carboxy-1,4-dihydropyridine;
2,6-dimethyl-3-methoxyethoxycarbonyl-4-(2-nitrophenyl)-5-carboxy-1,4-dihydropyridine;
2,6-dimethyl-3-methoxyethoxycarbonyl-4-(3-chlorophenyl)-5-carboxy-1,4-dihydropyridine;
2,6-dimethyl-3-methoxyethoxycarbonyl-4-(2-chlorophenyl)-5-carboxy-1,4-dihydropyridine;
1,6-dimethyl-3-methoxyethoxycarbonyl-4-(2,3-dichlorophenyl)-5-carboxy-1,4-dihydropyridine;
2,6-dimethyl-3-methoxyethoxycarbonyl-4-(4-methylphenyl)-5-carboxy-1,4-dihydropyridine;
2,6-dimethyl-3-methoxyethoxycarbonyl-4-(3-cyanophenyl)-5-carboxy-1,4-dihydropyridine;
2,6-dimethyl-3-methoxyethoxycarbonyl-4-(3-trifluoromethylphenyl)-5-carboxy-1,4-dihydropyridine;
2,6-dimethyl-3-methoxyethoxycarbonyl-4-(3-trifluoromethoxyphenyl)-5-carboxy-1,4-dihydropyridine;
2,6-dimethyl-3-methoxyethoxycarbonyl-4-(3-methoxyphenyl)-5-carboxy-1,4-dihydropyridine;
2,6-dimethyl-3-methoxyethoxycarbonyl-4-(2-thienyl)-5-carboxy-1,4-dihydropyridine;
2,6-dimethyl-3-methoxyethoxycarbonyl-4-(5-methylthien-2-yl)-5-carboxy-1,4-dihydropyridine;
2,6-dimethyl-3-cyano-4-(2-nitrophenyl)-5-carboxy-1,4-dihydropyridine;
(+)-2,6-dimethyl-3-cyano-4-(3-nitrophenyl)-5-carboxy-1,4-dihydropyridine, mp=225° C., $[\alpha]_D^{20} = +251.2°$, c=5, DMF;
2,6-dimethyl-3-cyano-4-(3-chlorophenyl)-5-carboxy-1,4-dihydropyridine;
2,6-dimethyl-3-cyano-4-(2-chlorophenyl)-5-carboxy-1,4-dihydropyridine;
2,6-dimethyl-3-cyano-4-(2,3-dichlorophenyl)-5-carboxy-1,4-dihydropyridine;
2,6-dimethyl-3-cyano-4-(4-methylphenyl)-5-carboxy-1,4-dihydropyridine;
2,6-dimethyl-3-cyano-4-(3-cyanophenyl)-5-carboxy-1,4-dihydropyridine;
2,6-dimethyl-3-cyano-4-(3-trifluoromethylphenyl)-5-carboxy-1,4-dihydropyridine;
2,6-dimethyl-3-cyano-4-(3-trifluoromethoxyphenyl)-5-carboxy-1,4-dihydropyridine;
2,6-dimethyl-3-cyano-4-(3-methoxyphenyl)-5-carboxy-1,4-dihydropyridine;
2,6-dimethyl-3-cyano-4-(2-thienyl)-5-carboxy-1,4-dihydropyridine;
2,6-dimethyl-3-cyano-4-(5-methylthien-2-yl)-5-carboxy-1,4-dihydropyridine;
2,6-dimethyl-3nitro-4-(2-nitrophenyl)-5-carboxy-1,4-dihydropyridine;
2,6-dimethyl-3-nitro-4-(3-nitrophenyl)-5-carboxy-1,4-dihydropyridine;
2,6-dimethyl-3-nitro-4-(3-chlorophenyl)-5-carboxy-1,4-dihydropyridine;

2,6-dimethyl-3-nitro-4-(2-chlorophenyl)-5-carboxy-1,4-dihydropyridine;
2,6-dimethyl-3-nitro-4-(2,3-dichlorophenyl)-5-carboxy-1,4-dihydropyridine;
2,6-dimethyl-3-nitro-4-(4-methylphenyl)-5-carboxy-1,4-dihydropyridine;
2,6-dimethyl-3-nitro-4-(3-nitrophenyl)-5-carboxy-1,4-dihydropyridine;
2,6-dimethyl-3-nitro-4-(3-trifluoromethylphenyl)-5-carboxy-1,4-dihydropyridine;
2,6-dimethyl-3-nitro-4-(3-trifluoromethoxyphenyl)-5-carboxy-1,4-dihydropyridine;
2,6-dimethyl-3-nitro-4-(3-methoxyphenyl)-5-carboxy-1,4-dihydropyridine;
2,6-dimethyl-3-nitro-4-(2-thienyl)-5-carboxy-1,4-dihydropyridine;
2,6-dimethyl-3-nitro-4-(5-methyl-2-thienyl)-5-carboxy-1,4-dihydropyridine;
2,6-dimethyl-3-carbomethoxy-4-(2-furanyl)-5-carboxy-1,4-dihydropyridine;
2,6-dimethyl-3-carboethoxy-4-(2-furanyl)-5-carboxy-1,4-dihydropyridine;
2,6-dimethyl-3-carboisopropoxy-4-(2-furanyl)-5-carboxy-1,4-dihydropyridine;
2,6-dimethyl-3-carboisobutoxy-4-(2-furanyl)-5-carboxy-1,4-dihydropyridine;
2,6-dimethyl-3-methylsulfonyl-4-(2-furanyl)-5-carboxy-1,4-dihydropyridine;
2,6-dimethyl-3-cyano-4-(2-furanyl)-5-carboxy-1,4-dihydropyridine;
2,6-dimethyl-3-nitro-4-(2-furanyl)-5-carboxy-1,4-dihydropyridine;
2,6-dimethyl-3-carbomethoxy-4-(2-pyridyl)-5-carboxy-1,4-dihydropyridine;
2,6-dimethyl-3-carboethoxy-4-(2-pyridyl)-5-carboxy-1,4-dihydropyridine;
2,6-dimethyl-3-carboisopropoxy-4-(2-pyridyl)-5-carboxy-1,4-dihydropyridine;
2,6-dimethyl-3-carboisobutoxy-4-(2-pyridyl)-5-carboxy-1,4-dihydropyridine;
2,6-dimethyl-3-methylsulfonyl-4-(2-pyridyl)-5-carboxy-1,4-dihydropyridine;
2,6-dimethyl-3-cyano-4-(2-pyridyl)-5-carboxy-1,4-dihydropyridine;
2,6-dimethyl-3-nitro-4-(2-pyridyl)-5-carboxy-1,4-dihydropyridine;
2,6-dimethyl-3-carbomethoxy-4-(4-benzodioxazolyl)-5-carboxy-1,4-dihydropyridine;
2,6-dimethyl-3-carboethoxy-4-(4-benzodioxazolyl)-5-carboxy-1,4-dihydropyridine;
2,6-dimethyl-3-carboisopropoxy-4-(4-benzodioxazolyl)-5-carboxy-1,4-dihydropyridine;
2,6-dimethyl-3-carboisobutoxy-4-(4-benzodioxazolyl)-5-carboxy-1,4-dihydropyridine;
2,6-dimethyl-3-methylsulfonyl-4-(4-benzodioxazolyl)-5-carboxy-1,4-dihydropyridine;
2,6-dimethyl-3-cyano-4-(4-benzodioxazolyl)-5-carboxy-1,4-dihydropyridine; and
2,6-dimethyl-3-nitro-4-(4-benzodioxazolyl)-5-carboxy-1,4-dihydropyridine.

(C) The mother liquors obtained in part (A) above are then evaporated, and the residue suspended in $H_2O$ (400 mL) containing NaOH (22 mL of 35% solution). The aqueous phase is then washed with $CH_2Cl_2$ (2×200 mL) and acidified with HCl (12N, 22 mL). The precipitate is then filtered, washed with water, and dried to obtain nearly pure (+)-2,6-dimethyl-3-carbomethoxy-4-(3-nitrophenyl)-5-carboxy-1,4-dihydropyridine.

(D) Similarly, proceeding as in part (C) above but substituting the mother liquors obtained in part (B) above for the mother liquor obtained from part (A), the corresponding compounds are prepared.

(E) Similarly, proceeding as in parts (A–B) but substituting cinchonidine for quinidine, the corresponding pure (+) and (−) isomers are obtained.

EXAMPLE 2

(Preparation of Cinchonidine Salts)

(A) A mixture of 2,6-dimethyl-3-carbomethoxy-4-(3-nitrophenyl)-5-carboxy-1,4-dihydropyridine (66.4 g, 0.1 mol) and cinchonidine (59 g, 0.2 mol) was dissolved in hot DMF (120 mL). When both compounds has dissolved, $H_2O$ (100 mL) was added and the solution allowed to cool for 24 hours under ambient conditions. The resulting precipitate was filtered, dried, and recrystallized from $DMF/H_2O$ (60:40) to yield the pure salt, mp=200–205°C. (One may also recrystallize the produce from EtOH or MeOH.)

The pure (+) dihydropyridine acid was obtained by dissolving 17.8 g of the cinchonidinium salt and NaOH (2.7 mL of 35% soln) in water (60 mL). The solution was extracted twice with $CH_2Cl_2$ (30 mL), then acidified with HCl (12N, 3.4 mL). The resulting precipitate was filtered, washed with $H_2O$, and dried. The dried product was rinsed with $Et_2O$ (2×50 mL) to yield pure (+)-2,6-dimethyl-3-carbomethoxy-4-(3-nitrophenyl)-5-carboxy-1,4-dihydropyridine (1), $[\alpha]_D^{20}=+20.3°$ (c=0.5, acetone), mp=202–203° C.

(B) Similarly, proceeding as in part (A) above but substituting the appropriate starting materials for 2,6-dimethyl-3-carbomethoxy-4-(3-nitrophenyl)-5-carboxy-1,4-dihydropyridine, the following optically resolved compounds are prepared:

2,6-dimethyl-3-carbomethoxy-4-(2-nitrophenyl)-5-carboxy-1,4-dihydropyridine;
2,6-dimethyl-3-carbomethoxy-4-(3-chlorophenyl)-5-carboxy-1,4-dihydropyridine;
2,6-dimethyl-3-carbomethoxy-4-(2-chlorophenyl)-5-carboxy- 1,4-dihydropyridine;
(−-2,6-dimethyl-3-carbomethoxy-4-(2,3-dichlorophenyl)-5-carboxy-1,4-dihydropyridine, mp=225° C., $[\alpha]_D^{20}=-28.5°$, c=5, DMF;
2,6-dimethyl-3-carbomethoxy-4-(4-methylphenyl)-5-carboxy-1,4-dihydropyridine;
2,6-dimethyl-3-carbomethoxy-4-(3-cyanophenyl)-5-carboxy-1,4-dihydropyridine;
2,6-dimethyl-3-carbomethoxy-4-(3-trifluoromethylphenyl)-5-carboxy-1,4-dihydropyridine;
2,6-dimethyl-3-carbomethoxy-4-(3-trifluoromethoxyphenyl)-5-carboxy-1,4-dihydropyridine;
2,6-dimethyl-3-carboethoxy-4-(2-nitrophenyl)-5-carboxy-1,4-dihydropyridine;
2,6-dimethyl-3-carboethoxy-4-(3-nitrophenyl)-5-carboxy-1,4-dihydropyridine;
2,6-dimethyl-3-carboethoxy-4-(3-chlorophenyl)-5-carboxy-1,4-dihydropyridine;
2,6-dimethyl-3-carboethoxy-4-(2-chlorophenyl)-5-carboxy-1,4-dihydropyridine;
2,6-dimethyl-3-carboethoxy-4-(2,3-dichlorophenyl)-5-carboxy-1,4-dihydropyridine;
2,6-dimethyl-3-carboethoxy-4-(4-methylphenyl)-5-carboxy-1,4-dihydropyridine;
2,6-dimethyl-3-carboethoxy-4-(3-cyanophenyl)-5-carboxy-1,4-dihydropyridine;

2,6-dimethyl-3-carboethoxy-4-(3-trifluoromethylphenyl)-5-carboxy-1,4-dihydropyridine;
2,6-dimethyl-3-carboethoxy-4-(3-trifluoromethoxyphenyl)-5-carboxy-1,4-dihydropyridine;
2,6-dimethyl-3-carboisopropoxy-4-(2-nitrophenyl)-5-carboxy-1,4-dihydropyridine;
(−)-2,6-dimethyl-3-carboisopropoxy-4-(3-nitrophenyl)-5-carboxy-1,4-dihydropyridine, mp=195° C., $[\alpha]_D^{20}=-28.9°$, c=5, DMF;
2,6-dimethyl-3-carboisopropoxy-4-(3-chlorophenyl)-5-carboxy-1,4dihydropyridine;
2,6-dimethyl-3-carboisopropoxy-4-(2-chlorophenyl)-5-carboxy-1,4-dihydropyridine;
2,6-dimethyl-3-carboisopropoxy-4-(2,3-dichlorophenyl)-5-carboxy-1,4-dihydropyridine;
2,6-dimethyl-3-carboisopropoxy-4-(4-methylphenyl)-5-carboxy-1,4-dihydropyridine;
2,6-dimethyl-3-carboisopropoxy-4-(3-cyanophenyl)-5-carboxy-1,4-dihydropyridine;
2,6-dimethyl-3-carboisopropoxy-4-(3-trifluoromethylphenyl)-5-carboxy-1,4-dihydropyridine;
2,6-dimethyl-3-carboisopropoxy-4-(3-trifluoromethoxyphenyl)-5-carboxy-1,4-dihydropyridine;
2,6-dimethyl-3-methylthio-4-(2-nitrophenyl)-5-carboxy-1,4-dihydropyridine;
2,6-dimethyl-3-methylthio-4-(3-nitrophenyl)-5-carboxy-1,4-dihydropyridine;
2,6-dimethyl-3-methylthio-4-(3-chlorophenyl)-5-carboxy-1,4-dihydropyridine;
2,6-dimethyl-3-methylthio-4-(2-chlorophenyl)-5-carboxy-1,4-dihydropyridine;
2,6-dimethyl-3-methylthio-4-(2,3-dichlorophenyl)-5-carboxy-1,4-dihydropyridine;
2,6-dimethyl-3-methylthio-4-(4-methylphenyl)-5-carboxy-1,4-dihydropyridine;
2,6-dimethyl-3-methylthio-4-(3-cyanophenyl)-5-carboxy-1,4-dihydropyridine;
2,6-dimethyl-3-methylthio-4-(3-trifluoromethylphenyl)-5-carboxy-1,4-dihydropyridine;
2,6-dimethyl-3-methylthio-4-(3-trifluoromethoxyphenyl)-5-carboxy-1,4-dihydropyridine;
2,6-dimethyl-3-ethylthio-4-(2-nitrophenyl)-5-carboxy-1,4-dihydropyridine;
2,6-dimethyl-3-ethylthio-4-(3-nitrophenyl)-5-carboxy-1,4-dihydropyridine;
2,6-dimethyl-3-ethylthio-4-(3-chlorophenyl)-5-carboxy-1,4-dihydropyridine;
2,6-dimethyl-3-ethylthio-4-(2-chlorophenyl)-5-carboxy-1,4-dihydropyridine;
2,6-dimethyl-3-ethylthio-4-(2,3-dichlorophenyl)-5-carboxy-1,4-dihydropyridine;
2,6-dimethyl-3-ethylthio-4-(4-methylphenyl)-5-carboxy-1,4-dihydropyridine;
2,6-dimethyl-3-ethylthio-4-(3-cyanophenyl)-5-carboxy-1,4-dihydropyridine;
2,6-dimethyl-3-ethylthio-4-(3-trifluoromethylphenyl)-5-carboxy-1,4-dihydropyridine;
2,6-dimethyl-3-ethylthio-4-(3-trifluoromethoxyphenyl)-5-carboxy-1,4-dihydropyridine;
2,6-dimethyl-3-isopropylthio-4-(2-nitrophenyl)-5-carboxy-1,4-dihydropyridine;
2,6-dimethyl-3-isopropylthio-4-(3-nitrophenyl)-5-carboxy-1,4-dihydropyridine;
2,6-dimethyl-3-isopropylthio-4-(3-chlorophenyl)-5-carboxy-1,4-dihydropyridine;
2,6-dimethyl-3-isopropylthio-4-(2-chlorophenyl)-5-carboxy-1,4-dihydropyridine;
2,6-dimethyl-3-isopropylthio-4-(2,3-dichlorophenyl)-5-carboxy-1,4-dihydropyridine;
2,6-dimethyl-3-isopropylthio-4-(4-methylphenyl)-5-carboxy-1,4-dihydropyridine;
2,6-dimethyl-3-isopropylthio-4-(3-cyanophenyl)-5-carboxy-1,4-dihydropyridine;
2,6-dimethyl-3-isopropylthio-4-(3-trifluoromethylphenyl)-5-carboxy-1,4-dihydropyridine;
2,6-dimethyl-3-isopropylthio-4-(3-trifluoromethoxyphenyl)-5-carboxy-1,4-dihydropyridine;
2,6-dimethyl-3-methylsulfonyl-4-(2-nitrophenyl)-5-carboxy-1,4-dihydropyridine;
2,6-dimethyl-3-methylsulfonyl-4-(3-nitrophenyl)-5-carboxy-1,4-dihydropyridine;
2,6-dimethyl-3-methylsulfonyl-4-(3-chlorophenyl)-5-carboxy-1,4-dihydropyridine;
2,6-dimethyl-3-methylsulfonyl-4-(2-chlorophenyl)-5-carboxy-1,4-dihydropyridine;
2,6-dimethyl-3-methylsulfonyl-4-(2,3-dichlorophenyl)-5-carboxy-1,4-dihydropyridine;
2,6-dimethyl-3-methylsulfonyl-4-(4-methylphenyl)-5-carboxy-1,4-dihydropyridine;
2,6-dimethyl-3-methylsulfonyl-4-(3-cyanophenyl)-5-carboxy-1,4-dihydropyridine;
2,6-dimethyl-3-methylsulfonyl-4-(3-trifluoromethylphenyl)-5-carboxy-1,4-dihydropyridine;
2,6-dimethyl-3-methylsulfonyl-4-(3-trifluoromethoxyphenyl)-5-carboxy-1,4-dihydropyridine;
2,6-dimethyl-3-ethylsulfonyl-4-(2-nitrophenyl)-5-carboxy-1,4-dihydropyridine;
2,6-dimethyl-3-ethylsulfonyl-4-(3-nitrophenyl)-5-carboxy-1,4-dihydropyridine;
2,6-dimethyl-3-ethylsulfonyl-4-(3-chlorophenyl)-5-carboxy-1,4-dihydropyridine;
2,6-dimethyl-3-ethylsulfonyl-4-(2-chlorophenyl)-5-carboxy-1,4-dihydropyridine;
2,6-dimethyl-3-ethylsulfonyl-4-(2,3-dichlorophenyl)-5-carboxy-1,4-dihydropyridine;
2,6-dimethyl-3-ethylsulfonyl-4-(4-methylphenyl)-5-carboxy-1,4-dihydropyridine;
2,6-dimethyl-3-ethylsulfonyl-4-(3-cyanophenyl)-5-carboxy-1,4-dihydropyridine;
2,6-dimethyl-3-ethylsulfonyl-4-(3-trifluoromethylphenyl)-5-carboxy-1,4-dihydropyridine;
2,6-dimethyl-3-ethylsulfonyl-4-(3-trifluoromethoxyphenyl)-5-carboxy-1,4-dihydropyridine;
2,6-dimethyl-3-isopropylsulfonyl-4-(2-nitrophenyl)-5-carboxy-1,4-dihydropyridine;
2,6-dimethyl-3-isopropylsulfonyl-4-(3-nitrophenyl)-5-carboxy-1,4-dihydropyridine;
2,6-dimethyl-3-isopropylsulfonyl-4-(3-chlorophenyl)-5-carboxy-1,4-dihydropyridine;
2,6-dimethyl-3-isopropylsulfonyl-4-(2-chlorophenyl)-5-carboxy-1,4-dihydropyridine;
2,6-dimethyl-3-isopropylsulfonyl-4-(2,3-dichlorophenyl)-5-carboxy-1,4-dihydropyridine;
2,6dimethyl-3-isopropylsulfonyl-4-(4-methylphenyl)-5-carboxy-1,4-dihydropyridine;
2,6-dimethyl-3-isopropylsulfonyl-4-(3-cyanophenyl)-5-carboxy-1,4-dihydropyridine;
2,6-dimethyl-3-isopropylsulfonyl-4-(3-trifluoromethylphenyl)-5-carboxy-1,4-dihydropyridine;
2,6-dimethyl-3-isopropylsulfonyl-4-(3-trifluoromethoxyphenyl)-5-carboxy-1,4-dihydropyridine;
2,6-dimethyl-3-methylsulfinyl-4-(2-nitrophenyl)-5-carboxy-1,4-dihydropyridine;
2,6-dimethyl-3-methylsulfinyl-4-(3-nitrophenyl)-5-carboxy-1,4-dihydropyridine;

2,6-dimethyl-3-methylsulfinyl-4-(3-chlorophenyl)-5-carboxy-1,4-dihydropyridine;
2,6-dimethyl-3-methylsulfinyl-4-(2-chlorophenyl)-5-carboxy-1,4-dihydropyridine;
2,6-dimethyl-3-methylsulfinyl-4-(2,3-dichlorophenyl)-5-carboxy-1,4-dihydropyridine;
2,6-dimethyl-3-methylsulfinyl-4-(4-methylphenyl)-5-carboxy-1,4-dihydropyridine;
2,6-dimethyl-3-methylsulfinyl-4-(3-cyanophenyl)-5-carboxy-1,4-dihydropyridine;
2,6-dimethyl-3-methylsulfinyl-4-(3-trifluoromethylphenyl)-5-carboxy-1,4-dihydropyridine;
2,6-dimethyl-3-methylsulfinyl-4-(3-trifluoromethoxyphenyl)-5-carboxy-1,4-dihydropyridine;
2,6-dimethyl-3-ethylsulfinyl-4-(2-nitrophenyl)-5-carboxy-1,4-dihydropyridine;
2,6-dimethyl-3-ethylsulfinyl-4-(3-nitrophenyl)-5-carboxy-1,4-dihydropyridine;
2,6-dimethyl-3-ethylsulfinyl-4-(3-chlorophenyl)-5-carboxy-1,4-dihydropyridine;
2,6-dimethyl-3-ethylsulfinyl-4-(2-chlorophenyl)-5-carboxy-1,4-dihydropyridine;
2,6-dimethyl-3-ethylsulfinyl-4-(2,3-dichlorophenyl)-5-carboxy-1,4-dihydropyridine;
2,6-dimethyl-3-ethylsulfinyl-4-(4-methylphenyl)-5-carboxy-1,4-dihydropyridine;
2,6-dimethyl-3-ethylsulfinyl-4-(3-cyanophenyl)-5-carboxy-1,4-dihydropyridine;
2,6-dimethyl-3-ethylsulfinyl-4-(3-trifluoromethylphenyl)-5-carboxy-1,4-dihydropyridine;
2,6-dimethyl-3-ethylsulfinyl-4-(3-trifluoromethoxyphenyl)-5-carboxy-1,4-dihydropyridine;
2,6-dimethyl-3-isopropylsulfinyl-4-(2-nitrophenyl)-5-carboxy-1,4-dihydropyridine;
2,6-dimethyl-3-isopropylsulfinyl-4-(3-nitrophenyl)-5-carboxy-1,4-dihydropyridine;
2,6-dimethyl-3-isopropylsulfinyl-4-(3-chlorophenyl)-5-carboxy-1,4-dihydropyridine;
2,6-dimethyl-3-isopropylsulfinyl-4-(2-chlorophenyl)-5-carboxy-1,4-dihydropyridine;
2,6-dimethyl-3-isopropylsulfinyl-4-(2,3-dichlorophenyl)-5-carboxy-1,4-dihydropyridine;
2,6-dimethyl-3-isopropylsulfinyl-4-(4-methylphenyl)-5-carboxy-1,4-dihydropyridine;
2,6-dimethyl-3-isopropylsulfinyl-4-(3-cyanophenyl)-5-carboxy-1,4-dihydropyridine;
2,6-dimethyl-3-isopropylsulfinyl-4-(3-trifluoromethylphenyl)-5-carboxy-1,4-dihydropyridine;
2,6-dimethyl-3-isopropylsulfinyl-4-(3-trifluoromethoxyphenyl)- 5-carboxy-1,4-dihydropyridine;
2,6-dimethyl-3-methoxyethoxycarbonyl-4-(2-nitrophenyl)-5-carboxy-1,4-dihydropyridine;
2,6-dimethyl-3-methoxyethoxycarbonyl-4-(3-chlorophenyl)-5-carboxy-1,4-dihydropyridine;
2,6-dimethyl-3-methoxyethoxycarbonyl-4-(2-chlorophenyl)-5-carboxy-1,4-dihydropyridine;
2,6-dimethyl-3-methoxyethoxycarbonyl-4-(2,3-dichlorophenyl)-5-carboxy-1,4-dihydropyridine;
2,6-dimethyl-3-methoxyethoxycarbonyl-4-(4-methylphenyl)-5-carboxy-1,4-dihydropyridine;
2,6-dimethyl-3-methoxyethoxycarbonyl-4-(3-cyanophenyl)-5-carboxy-1,4-dihydropyridine;
2,6-dimethyl-3-methoxyethoxycarbonyl-4-(3-trifluoromethylphenyl)-5-carboxy-1,4-dihydropyridine;
2,6-dimethyl-3-methoxyethoxycarbonyl-4-(3-trifluoromethoxyphenyl-5-carboxy-1,4-dihydropyridine;
2,6-dimethyl-3-methoxyethoxycarbonyl-4-(3-methoxyphenyl)-5-carboxy-1,4-dihydropyridine;
2,6-dimethyl-3-methoxyethoxycarbonyl-4-(2-thienyl)-5-carboxy-1,4-dihydropyridine;
2,6-dimethyl-3-methoxyethoxycarbonyl-4-(5-methylthien-2-yl)-5-carboxy-1,4-dihydropyridine;
2,6-dimethyl-3-cyano-4-(2-nitrophenyl)-5-carboxy-1,4-dihydropyridine;
2,6-dimethyl-3-cyano-4-(3-nitrophenyl)-5-carboxy-1,4-dihydropyridine;
2,6-dimethyl-3-cyano-4-(3-chlorophenyl)-5-carboxy-1,4-dihydropyridine:
2,6-dimethyl-3-cyano-4-(2-chlorophenyl)-5-carboxy-1,4-dihydropyridine;
2,6-dimethyl-3-cyano-4-(2,3-dichlorophenyl)-5-carboxy-1,4-dihydropyridine;
2,6-dimethyl-3-cyano-4-(4-methylphenyl)-5-carboxy-1,4-dihydropyridine;
2,6-dimethyl-3-cyano-4-(3-cyanophenyl)-5-carboxy-1,4-dihydropyridine;
2,6-dimethyl-3-cyano-4-(3-trifluoromethylphenyl)-5-carboxy-1,4-dihydropyridine;
2,6-dimethyl-3-cyano-4-(3-trifluoromethoxyphenyl)-5-carboxy-1,4-dihydropyridine;
2,6-dimethyl-3-cyano-4-(3-methoxyphenyl)-5-carboxy-1,4-dihydropyridine;
2,6-dimethyl-3-cyano-4-(2-thienyl)-5-carboxy-1,4-dihydropyridine; and
2,6-dimethyl-3-cyano-4-(5-methylthien-2-yl)-5-carboxy-1,4-dihydropyridine.

(C) The mother liquor obtained in part (A) above was then evaporated, and the residue suspended in H$_2$O (400 mL) containing NaOH (22 mL of 35% solution). The aqueous phase was washed with CH$_2$Cl$_2$ (2×200 mL) and acidified with HCl (12N, 22 mL). The precipitate was filtered, washed with water, and dried to obtain nearly pure (−)-2,6-dimethyl-3-carbomethoxy-4-(3-nitrophenyl)-5-carboxy-1,4-dihydropyridine, $[\alpha]_D^{20} = -17°$ (c=0.5, acetone). This acid (10 g) was mixed with cinchonine (8.9 g) and dissolved in hot EtOH (100 mL). When both compounds were nearly solubilized, the mixture was allowed to stand overnight. The resulting precipitate was filtered, acidified, washed and dried to yield pure (−) acid, $[\alpha]_D^{20} = -20.4°$ (c=0.5, acetone).

(D) Similarly, proceeding as in part (C) above but substituting the mother liquors obtained in part (B) above for the mother liquor obtained from part (A), the corresponding compounds are prepared.

EXAMPLE 3

(Preparation of Active Compounds)

(A) (1) A solution of (+)-2,6-dimethyl-3-methoxycarbonyl-4-(3-nitrophenyl-5-carboxy-1,4-dihydropyridine ($[\alpha]_D = +27.5°$, 8.0 g) in CH$_2$Cl$_2$ at 0° C. was treated with PCl$_5$ (5.3 g). To this mixture was added a solution of (R)-4-(2,2-dimethyl-1,3-dioxolan-4-yl)methoxyphenylethan-2-ol (6.4 g, $[\alpha]_D = +9.11°$ in CHCl$_3$) and triethylamine (3.8 mL) in CH$_2$Cl$_2$ to yield 2,6-dimethyl-3-methoxycarbonyl-4-(3-nitrophenyl)-5-(2-[4-(2,2-dimethyl-1,3-dioxolan-4-yl)methoxyphenyl]ethoxycarbonyl)-1,4-dihydropyridine.

(2) A solution of 21 g of 2,6-dimethyl-3-methoxycarbonyl-4-(3-nitrophenyl)-5-(2-[4-(2,2-dimethyl-1,3-dioxolan-4-yl)methoxyphenyl]ethoxycarbonyl)-1,4-dihydropyridine in 150 mL of acetone and 50 mL of water is treated with 10 mL of hydrochloric acid and the mixture heated at reflux for 6 h. Water (500 mL) is added and the mixture was extracted with ether. The ether layer is dried over Na$_2$SO$_4$ and evaporated to an oil which is purified by medium pressure chromatography on silica gel (90% ethyl acetate-hexane) to give 2,6-dimethyl-3-methoxycarbonyl-4-(3-nitrophenyl)-5-(2-[4-(2,3-dihydroxypropoxy)phenyl]ethoxycarbonyl)-1,4-dihydropyridine, m.p. 117–118° C., $[\alpha]_D = -33.5°$.

(B) Similarly, proceeding as in part (A)(1) above but substituting ethanol, isopropanol, or N-(2-hydroxyethyl)-N-benzyl-N-methylamine for 4-(2,2-dimethyl-1,3-dioxolan-4-yl)methoxyphenylethan-2ol, the following optically active compounds are prepared:

2,6-dimethyl-3-methoxycarbonyl-4-(3-nitrophenyl)-5-ethoxycarbonyl-1,4-dihydropyridine;
2,6-dimethyl-3-methoxycarbonyl-4-(3-nitrophenyl)-5-isopropoxycarbonyl-1,4-dihydropyridine; and
2,6-dimethyl-3-methoxycarbonyl-4-(3-nitrophenyl)-5-[ 2-(N-benzyl-N-methylamino)ethoxycarbonyl]-1,4-dihydropyridine.

(C) Similarly, proceeding as in parts (A)(1) and (B) above but substituting (+)-2,6-dimethyl-3-methoxysulfonyl-4-(3-nitrophenyl)-5-carboxy-1,4-dihydropyridine, (−)-2,6-dimethyl-3-methoxysulfonyl-4-(3-nitrophenyl)-5-carboxy-1,4-dihydropyridine, (+)-2,6-dimethyl-3-dimethylphosphonyl-4-(3-nitrophenyl)-5-carboxy-1,4-dihydropyridine, (−)-2,6-dimethyl-3-dimethylphosphonyl-4-(3-nitrophenyl)-5-carboxy-1,4-dihydropyridine, (+)-2,6-dimethyl-3-diethylphosphonyl-4-(3-nitrophenyl)-5-carboxy-1,4-dihydropyridine, (−)-2,6-dimethyl-3-diisopropylphosphonyl-4-(3-nitrophenyl)-5-carboxy-1,4-dihydropyridine, (+)-2,6-dimethyl-3-nitro-4-(2-trifluoromethylphenyl)-5-carboxy-1,4-dihydropyridine, (−)-2,6-dimethyl-3-nitro-4-(2-trifluoromethylphenyl)-5-carboxy-1,4-dihydropyridine, (+)-2,6-dimethyl-3-nitro-4-(4-benzodioxazolyl)-5-carboxy-1,4-dihydropyridine, (−)-2,6-dimethyl-3-nitro-4-(4-benzodioxazolyl)-5-carboxy-1,4-dihydropyridine, (+)-2,6-dimethyl-3-cyano-4-(2-trifluoromethylphenyl)-5-carboxy-1,4-dihydropyridine, or (−)-2,6-dimethyl-3-cyano-4-(2-trifluoromethylphenyl)-5-carboxy-1,4-dihydropyridine, for (+)-2,6-dimethyl-3-methoxycarbonyl-4-(3-nitrophenyl)-5-carboxy-1,4-dihydropyridine, and using methanol, ethanol, isopropanol, the following compounds are prepared:

(+)-2,6-dimethyl-3-methoxysulfonyl-4-(3nitrophenyl)-5-carbomethoxy-1,4-dihydropyridine;
(−)-2,6-dimethyl-3-methoxysulfonyl-4-(3-nitrophenyl)-5-carbomethoxy-1,4-dihydropyridine;
(+)-2,6-dimethyl-3-nitro-4-(2-trifluoromethylphenyl)-5-carbomethoxy-1,4-dihydropyridine;
(−)-2,6-dimethyl-3-nitro-4-(2-trifluoromethylphenyl)-5-carbomethoxy-1,4-dihydropyridine;
(+)-2,6-dimethyl-3-nitro-4-(4-benzodioxazolyl)-5-carbomethoxy-1,4-dihydropyridine;
(−)-2,6-dimethyl-3-nitro-4-(4-benzodioxazolyl)-5-carboisopropoxy-1,4-dihydropyridine;
(+)-2,6-dimethyl-3-cyano-4-(2-trifluoromethylphenyl)-5-carbomethoxy-1,4-dihydropyridine;
(−)-2,6-dimethyl-3-cyano-4-(2-trifluoromethylphenyl)-5-carbomethoxy-1,4-dihydropyridine;
(+)-2,6-dimethyl-3-methoxysulfonyl-4-(3-nitrophenyl)-5-carboethoxy-1,4-dihydropyridine;
(−)-2,6-dimethyl-3-methoxysulfonyl-4-(3-nitrophenyl)-5-carboethoxy-1,4-dihydropyridine;
(30     )-2,6-dimethyl-3-nitro-4-(2-trifluoromethylphenyl)-5-carboethoxy-1,4-dihydropyridine;
(−)-2,6-dimethyl-3-nitro-4-(2-trifluoromethylphenyl)-5-carboethoxy-1,4-dihydropyridine;
(+)-2,6-dimethyl-3-nitro-4-(4-benzodioxazolyl)-5-carboethoxy-1,4-dihydropyridine;
(−)-2,6-dimethyl-3-nitro-4-(4-benzodioxazolyl)-5-carboethoxy-1,4-dihydropyridine;
(+)-2,6-dimethyl-3-cyano-4-(2-trifluoromethylphenyl)-5-carboethoxy-1,4-dihydropyridine;
(−)-2,6-dimethyl-3-cyano-4-(2-trifluoromethylphenyl)-5-carboethoxy-1,4-dihydropyridine;
(+)-2,6-dimethyl-3-methoxysulfonyl-4-(3-nitrophenyl)-5-carboisopropoxy-1,4-dihydropyridine;
(−)-2,6-dimethyl-3-methoxysulfonyl-4-(3-nitrophenyl)-5-carboisopropoxy-1,4-dihydropyridine;
(+)-2,6-dimethyl-3-nitro-4-(2-trifluoromethylphenyl)-5-carboisopropoxy-1,4-dihydropyridine;
(−)-2,6-dimethyl-3-nitro-4-(2-trifluoromethylphenyl)-5-carboisopropoxy-1,4-dihydropyridine;
(+)-2,6-dimethyl-3-nitro-4-(4-benzodioxazolyl)-5-carboisopropoxy-1,4-dihydropyridine;
(−)-2,6-dimethyl-3-nitro-4-(4-benzodioxazolyl)-5-carboisopropoxy-1,4-dihydropyridine;
(+)-2,6-dimethyl-3-cyano-4-(2-trifluoromethylphenyl)- 5-carboisopropoxy-1,4-dihydropyridine;
(−)-2,6-dimethyl-3-cyano-4-(2-trifluoromethylphenyl)-5-carboisopropoxy-1,4-dihydropyridine;
(+)-2,6-dimethyl-3-dimethylphosphonyl-4-(3-nitrophenyl)-5-carbomethoxy-1,4-dihydropyridine;
(−)-2,6-dimethyl-3-dimethylphosphonyl-4-(3-nitrophenyl)-5-carbomethoxy-1,4-dihydropyridine;
(+)-2,6-dimethyl-3-diethylphosphonyl-4-(3-nitrophenyl)-5-carbomethoxy-1,4-dihydropyridine; and
(−)-2,6-dimethyl-3-diisopropylphosphonyl-4-(3-nitrophenyl)-5-carbomethoxy-1,4-dihydropyridine.

What is claimed:

1. A process for preparing the optical isomers of a compound of formula 1

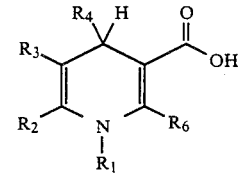

wherein
R$_1$ is H or lower alkyl;
R$_2$ and R$_6$ are each independently lower alkyl, aryl, or arylalkyl;
R$_3$ is CN, NO$_2$, CO$_2$R$_5$, CONHR$_5$, SO$_2$R$_5$, or P(O)(OR$_5$)$_2$, where R$_5$ is lower alkyl, lower alkoxyalkyl, alkoxyalkyl, aryl, or arylalkyl;
R$_4$ is aryl, heterocyclyl, or fused-ring heterocyclyl, optionally substituted with one, two, or three substituents independently selected from halo, NO$_2$, CN, lower alkyl, lower alkoxy, lower alkylamino, CF$_3$, OCH$_2$F, and OCF$_3$; which process comprises:
dissolving said compound of formula 1 and an optically active amine base in a ratio of about 1:2 to about 2:1, wherein said amine is cinchonidine, quinidine, strychnine, brucine, morphine, d-α-phenylethylamine, l-arginine, dehydroabietylamine, cinchonicine, cinchonine, 1-2-amino-1-propanol, d-amphetamine, glucosamine, conessine, or anabasine in a mixture of water and a solvent selected from dimethyl formamide, ethanol, and acetonitrile at a temperature between about 50° C. and the reflux temperature of said solvent for about 2 to about 30 minutes to form a racemic salt solution which is about 10% to about 50% water; and allowing one optically active salt of said compound of formula 1 to crystallize.

2. The process of claim 1 wherein said solvent is dimethyl formamide.

3. The process of claim 1 wherein said amine is cinchonidine, cinchonine or quinidine.

* * * * *